United States Patent
Lee et al.

(10) Patent No.: US 6,306,169 B1
(45) Date of Patent: Oct. 23, 2001

(54) TISSUE IMPLANT

(75) Inventors: David Alan Lee, St. Albans; Daniel Lawrence Bader, London; Myra Deborah Stephens, Edgware, all of (GB)

(73) Assignees: Abonetics Ltd. (GB); University College London (GB)

( * ) Notice: Subject to any disclaimer, the term of this patent is extended or adjusted under 35 U.S.C. 154(b) by 0 days.

(21) Appl. No.: 09/188,165

(22) Filed: Nov. 9, 1998

Related U.S. Application Data (63) Continuation of application No. PCT/GB98/00673, filed on Mar. 6, 1998.

(30) Foreign Application Priority Data

Mar. 7, 1997 (GB) .................................................. 9704749

(51) Int. Cl.[7] .................................. A61F 2/02; A61F 2/28
(52) U.S. Cl. ........................................ 623/11.11; 623/16.11
(58) Field of Search ................................... 623/11, 16, 17, 623/18, 11.11, 16.11, 17.11, 17.12, 18.11

(56) References Cited

U.S. PATENT DOCUMENTS

| | | | |
|---|---|---|---|
| 5,916,585 | * | 7/1999 | Cook et al. ............................ 424/426 |
| 5,939,323 | * | 8/1999 | Valentini et al. ..................... 435/395 |
| 5,944,754 | * | 8/1999 | Vacanti .................................. 623/11 |

FOREIGN PATENT DOCUMENTS

| | | |
|---|---|---|
| 2 657 352 A1 | 7/1991 | (FR) . |
| WO 89/00413 | 1/1989 | (WO) . |
| WO 90/09769 | 9/1990 | (WO) . |
| WO 91/16867 | 11/1991 | (WO) . |
| WO 93/11723 | 6/1993 | (WO) . |
| WO 95/31157 | 11/1995 | (WO) . |
| WO 95/32623 | 12/1995 | (WO) . |
| WO 96/25961 | 8/1996 | (WO) . |

OTHER PUBLICATIONS

Archer, C.W., et al., "Phenotypic modulation in sub–populations of human articular chondrocytes in vitro," *J. Cell Sci.* 97 Part 2:361–371 (Oct. 1990).

Bader, D.L., et al., "The effects of leucocyte elastase on the mechanical properties of adult human articular cartilage in tension," *Biochim. Biophys. Acta* 677:103–108 (Sep. 1981).

Bader, D.L., et al., "The effects of selective matrix degradation on the short–term compressive properties of adult human articular cartilage," *Biochim. Biophys. Acta* 1116:147–154 (Apr. 1992).

Bader, D.L., et al., "The short–term compressive properties of adult human articular cartilage," *Bio–Med. Mater Eng.* 4:245–256 (Jul. 1994).

Freed, L.E., et al., "Neocartilage formation in vitro and in vivo using cells cultured on synthetic biodegradable polymers," *J. Biomed. Mater. Res.* 27:11–23 (Jan. 1993).

Lee, D.A., et al., "The control of cell division in articular chondrocytes," *Osteoarthritis Cartilage* 1:137–146 (Apr. 1993).

Lee, D.A., and Bader, D.L., "The development and characterization of an in vitro system to study strain–induced cell formation in isolated chondrocytes," *In Vitro Cell. Dev. Biol. Anim.* 31:828–835 (Dec. 1995).

Lee, D.A., and Bader, D.L., "Compression Strains at Physiological Frequencies Influence the Metabolism of Chondrocytes Seeded in Agarose," *J. Orthop. Res.* 15:181–188 (Mar. 1997).

International Search Report for International Application No. PCT/GB98/00673, mailed Aug. 12, 1998.

Dialog file 351, Derwent World Patents Index, English language abstract for FR 2 657 352 A1, WPI Accession No. 91–283611.

* cited by examiner

*Primary Examiner*—Corrine McDermott
*Assistant Examiner*—Hieu Phan
(74) *Attorney, Agent, or Firm*—Sterne, Kessler, Goldstein & Fox, P.L.L.C.

(57) ABSTRACT

A biomechanical implant is described which comprises at least two matrix components, the first matrix component being composed of collagen with a porous macrostructure with the ability to withstand tensile or shear forces, the second matrix component being a hydrated alginate gel which substantially fills the porous macrostructure of the first component and exerts a swelling pressure, the implant additionally comprising a population of cells comprising chondrocytes, fibrochondrocytes, fibroblasts or osteoblasts, or precursors thereof.

22 Claims, 10 Drawing Sheets

TISSUE IMPLANT

The present application is a continuation of international application PCT/GB98/00673, filed Mar. 6, 1998, said PCT/GB98/00673 claims the benefit of Great Britain Application No. 9704749.2, filed Mar. 7, 1997.

BACKGROUND OF THE INVENTION

1. Field of the Invention

The present invention relates to a tissue implant for use in damaged load-bearing cartilaginous tissue, such as the meniscus and articular cartilage.

2. Related Art

Many non-calcified skeletal connective tissues such as articular cartilage, menisci, ligaments, tendons and intervertebral disc have a mechanical function and, as such, are subjected to dynamic mechanical loading during physiological activity. For example, joint forces are considerable during normal physiological activities and commonly exceed 2000 N or three times body weight and occur repetitively approximately 1 million times per year. Thus articular cartilage will be commonly subjected to contact stresses exceeding 5 MPa.

The cartilaginous tissues are composed of cells embedded within an extensive extracellular matrix. The functional behaviour of these tissues is best understood when it is considered as biphasic consisting of a fluid phase of interstitial water containing dissolved inorganic salts and a solid phase containing the collagen-proteoglycan organic solid matrix. The two phases together permit fluid flow through the permeable solid phase. It is the physicochemical interaction of the various components of the extracellular matrix which is responsible for the mechanical properties of the healthy tissues. For example in articular cartilage, there is a physico-chemical equilibrium between the osmotic swelling pressure ($P_{swelling}$) of the proteoglycan gel which is balanced by the hydrostatic pressures ($P_{elastic}$) due to the tensile stresses generated within the collagen fibre network. This balance exists even in unloaded articular cartilage. It is altered when the tissue is loaded in compression by an applied hydrostatic pressure ($P_{applied}$) resulting in a net pressure differential ($\Delta p$) and fluid flow away from the compressed tissue. The appropriate equation is given by $$\Delta p = P_{applied} + (P_{elastic} - P_{swelling})$$

This fluid flow will result in an increased proteoglycan concentration within the tissue and a change in the relative magnitudes of the stresses in the two solid components of articular cartilage. If the compressive load remains constant the rate of fluid flow decreases with time and eventually reduces to zero at a new state of equilibrium. This time-dependent creep behaviour is characteristic of all viscoelastic soft tissues.

The cells, although occupying less than 10% of the tissue volume, are necessary for the synthesis and maintenance of matrix levels and are, therefore, crucial to the structural integrity and function of the tissue. It is known that the cells, whether chondrocytes in cartilage, fibrochondrocytes in menisci, or tenocytes and fibroblasts in tendon and ligament respectively, are able to alter their metabolic activity in response to applied loads. Both the level of strain applied and the dynamic frequency are known to be important in determining this response. These processes are believed to be major factors in determining cellular activity in these tissues.

The mechanisms by which cells detect and respond to mechanical load are termed mechanotransduction pathways and are complex and poorly understood. mechanotransduction events may be resolved into extracellular components including cell deformation, hydrostatic pressures and streaming potentials, followed by intracellular signalling events such as intracellular calcium fluxes, cAMP production and cytoskeletal alterations which finally lead to altered effector cell response. However, understanding such mechanisms has been complicated by the need to investigate the processes at a number of different levels, including the cellular level.

Injuries to soft tissues are extremely common in hospital clinics. Indeed, soft tissue replacements amount to an estimated 35% of the world market for all medical devices (Materials Technology Foresight in Biomaterials, Institute of Materials, London (1995).

In the case of articular cartilage and knee menisci, traumatic damage is common in young active people. Natural repair is often poor due to limited vascularity. If untreated, damage commonly leads to progressive degenerative changes, such as osteoarthritis, in the injured tissue and associated structures. Current solutions, include the use of artificial joints but these implants have a relatively short lifespan of 12–15 years with subsequent replacements lasting for shorter periods. This is a special problem for patients who have received an implant early in life.

There have been many options proposed for the repair of soft tissues. These generally involve synthetic materials, biological materials or a combination of the two. The former solutions have the advantages of providing a structure which is immunologically acceptable and with the mechanical integrity required of load bearing structures. However their instability in the body leads to relatively poor long term performance. Biological solutions traditionally involve autografts, allografts or xenografts, depending on their source of tissues. Each of these options has proved to be far from ideal with, for example, autografts leading to donor site morbidity and allografts and xenografts leading to graft rejection.

Other common solutions involve augmentation devices incorporating both synthetic structures and biological grafts. These devices depend on tissue ingrowth and regeneration induced by the successful transfer of stress from the synthetic material to the natural tissues. This stress transfer process would need to change with time after implantation as the tissue regenerates. Clinical reports are not generally convincing due to, for example, the inadequate initial performance of the synthetic component of the augmentation device.

Commonly used procedures for treatment of articular cartilage lesions include the Pridie technique which involves drilling or abrasion of the joint surface to release repair cells which form a fibrocartilaginous repair tissue. Other procedures involve the use of carbon fibre rods or mats associated with drilling and the use of allografts and xenografts. These techniques lead to the formation of soft fibrocartilaginous tissue which has limited long-term stability. Options for the treatment of damaged menisci currently include, surgery to remove the damaged portion of meniscus (20 years ago, before the meniscus was better understood, damaged menisci were removed completely), implantation of a plastic meniscus or using fibrin-glue to glue back the torn portion of meniscus. However, in plastic meniscal implants the use of hydrogels is often inadequate and there are problems with shear/stress forces on the implant. The use of fibrin glue is also unsatisfactory because the meniscus still contains a point of weakness and is a non-homogeneous anisotropic structure.

The relative failure of many surgical, synthetic and graft solutions has led to the growing interest in the development of cell-seeded repair systems for solving a number of clinical problems related to connective tissues such as articular cartilage, menisci and ligaments. These systems have also been called tissue-engineered repair systems. Typically autologous or allogenic cells are isolated from a tissue biopsy removed from a site remote from the injury. The cells are expanded in cell culture and seeded in a suitable 3D resorbable scaffold material, which when implanted into the defective or damaged site elicit a biological repair.

There are some reports describing in vitro and in vivo evaluation of cell-engineered systems for repair of load-bearing cartilaginous tissues. Examples of such systems have been described by Brittberg et al (*New England Journal of Medicine* 331 889–95 (1994)), WO 89/00413, WO 90/09769, WO 91/16867, WO 90/12603, WO 95/31157 and Paige et al (*Plastic and Reconstructive Surgery* 97(1) 168–180 (1996)).

Brittberg et al describe a procedure in which autologous chondrocytes, expanded in culture, are transferred into the defect. This procedure does not involve a scaffold material and thus a periosteal graft is required, with associated donor site morbidity, to retain the cells within the defect. The implanted cells are denuded of matrix and therefore have no mechanical integrity on implantation. Also the technique is only suitable for lesions which do not include the subchondral bone.

Stone (WO 89/00413, WO 90/09769, WO 91/16867) describe prostheses for the intervertebral disc, meniscus or other similar tissue. Each prosthesis is said to include a dry, porous, volume matrix of biocompatible and bioresorbable fibres. These are described as being interspersed with glycosaminoglycan molecules, which may provide attachment sites for cross-links to the fibres. The shape of such devices can either be manufactured to replicate the outer surface contour of the biological structure which it is designed to replace, or can be manufactured to a larger shape and trimmed down to size. For long term in vivo performance, these prostheses require the infiltration of functional fibrochondrocytes to provide a scaffold for the regenerating tissue structure. However, this prosthesis is not cell seeded and thus does not depend upon the use of seeded cells into the scaffold prior to implantation. Additionally, the nature of the mechanical interaction has not been specified.

The choice of biomaterials has to date been largely empirical based on biocompatibility and the maintenance of cell morphology and function. Additionally, the structural design of devices has been generally ignored. Materials such as collagen in various forms, poly-1-lactic acid and alginates have been employed. Most of the post implantation analysis has involved histological and biochemical analysis of repair tissue, with only a few reports assessing its mechanical integrity. The mechanical integrity of the device pre-implantation has been largely ignored. For example, Vacanti (WO 90/12603) and Kim et al (Plastic and Reconstructive Surgery 94(2) 233–237 (1994)) describe a method in which chondrocytes are seeded onto a bioresorbable polymer scaffold for transfer into a cartilaginous defect. Whilst the constructs may have a defined shape and size, the mechanical properties do not approach that of articular cartilage. The compressive modulus of articular cartilage is approximately 5–10 MPa. Problems associated with ensuring an initial even cell density and maintenance of chondrocytes phenotype are not addressed. The application of a coating to the scaffold was proposed but only to induce cell attachment. The method relies upon the synthesis of sufficient cartilaginous matrix to fill voids within the scaffold before any significant mechanical integrity is achieved.

Paige et al (Plastic and Reconstructive Surgery 97(1) 168–180 (1996)) propose the use of cells embedded in alginate alone. However, these devices are approximately one hundred times less stiff than cartilage raising questions about the mechanical functionality of the device.

WO 95/31157 relates to an anatomically specific bioresorbable device for healing of voids in soft tissues, such as in articular cartilage and the associated subchondral bone. The device is described as being an internal three-dimensional structure in fibrous form, termed the macrostructure, with voids which are partially or totally filled with a polymer gel, forming a microstructure. The gel provides a carrier material for selected chondrocytes and in conjunction with chemical mediators into the cartilage region of the device to enhance tissue regeneration. The gel phase is designed to be resorbed after 72 hours in vivo. This prosthesis, therefore, only depends upon the seeded microstructure to deliver the cells and to enable the short term transfer of cells on to the fibrous scaffold. The design does not depend upon the total filling of the voids by the microstructure. There is no consideration or mention of the physicochemical interaction of the macrostructure and the microstructure or the resulting mechanical integrity of the prosthesis at any time following implantation.

None of the aforementioned methods will produce a construct with a mechanical function which resembles that possessed by the tissues to be repaired. In addition none of the aforementioned methods address the transfer of mechanical load to cells within the device leading to mechanotransduction-induced desired cell response. It has now been discovered that an approach which considers both the mechanical and biological aspects of implants for repair of damaged load-bearing connective tissue can provide a superior device for implantation.

BRIEF SUMMARY OF THE INVENTION

According to a first aspect of the present invention there is provided a biomechanical implant comprising at least two matrix components, the first matrix component having a porous macrostructure with the ability to withstand tensile or shear forces, the second matrix component being a hydrated gel which substantially fills the porous macrostructure of the first component and exerts a swelling pressure. The implant additionally comprises a population of animal cells having a differentiated phenotype or having an undifferentiated phenotype with the potential to differentiate into such cells.

DETAILED DESCRIPTION OF THE INVENTION

The biomechanical implants according to the present invention are advantageous in that they provide a composite construct with mechanical properties under compressive loading which are greater than the sum of the compressive properties of the two components individually. In this manner, the composite construct may contribute to the restoration of the biomechanical function of the damaged tissue immediately post-implantation.

The implant may be a full or partial replacement for tissues where there is a mechanical interaction in both the loaded and unloaded states sufficient to set up an equilibrium between major matrix components, such as those with a mechanical function, where compression is the predominant type of loading. Suitable tissues for repair can include but are not limited to tissues such as cartilage, temporomandibular joint menisci, knee menisci and intervertebral discs.

The first matrix component may suitably be composed of a biodegradable or bioresorbable polymer such as collagen, gelatin, poly-L-lactic acid, poly-glycolic acid, polycaprolactone, polyhydroxybutarate, polyanhydrides and copolymers of the above. However, the specific use of non-resorbable polymeric components, or of non-polymeric resorbable components such as soluble bioglasses is not precluded. The first matrix component may preferably be composed of collagen.

The mechanical properties, antigenicity and degradation rate of the polymers comprising the first matrix component can be modified by the use of crosslinking agents such as glutaraldehyde, formaldehyde, tissue transglutaminase and acid aldehyde or by heat treatment. The polymers forming the first matrix component can be modified by alteration to the surface properties of the polymer. This can be achieved by coating with components known to influence cell attachment and differentiation such as hydroxyapatite, fibronectin, collagen, vitronectin, hyaluronan, proteoglycans, glycosaminoglycans or RGD (Arg-Gly-Asp) tripeptide cell attachment sequence. Coating may be restricted to specified regions of the first matrix component. Alternatively, attachment can be influenced by specific surface ultrastructural features such as grooves or microporosities within the range 0.1–50 µm, suitably 1–25 µm, preferably 3–10 µm.

The polymeric components forming the first matrix component preferably may possess a porous macrostructure consisting of interconnecting channels. The average size of the pores may range from 10–1000 µm, suitably 30–250 µm, preferably 50–150 µm with a total porosity ranging from 50–98%, suitably 60–95%, preferably 70–90%. The macrostructure can therefore be in the form of woven or non-woven fibres, sponges or foams, or a series of plates or sheets joined by interconnecting strands, fibres or adjoining plates. The macrostructure of the first matrix component can be non-homogeneous in terms of porosity, pore size and/or predominant polymeric fibre/plate/sheet orientation.

In biomechanical implants to replace articular cartilage, the dimensions of the first matrix component may be approximately 0.05–6 mm, suitably 0.0754 mm, preferably 0.1–3 mm in thickness, corresponding to the thickness of articular cartilage. The other dimensions of the construct suitably may correspond to the dimensions of the defect to be repaired. The macrostructure conveniently possesses a surface zone with an orientation predominantly parallel to the surface. This zone preferably corresponds to the natural superficial zone of the cartilage, thereby representing approximately 10–20% of the total thickness of the construct in the range 0.005–1.2 mm, suitably 0.0075–0.8 mm, preferably 0.1–0.6 mm. The surface zone also preferably may possess a relatively low porosity, within the range 50–98%, suitably 60–95%, preferably 65–80% with average pore size between 10–1000 µm, suitably 30–250 µm, preferably 50–100 µm. The predominant macrostructural organisation within the remainder of the construct depth may be suitably perpendicular to the surface with a porosity between 50–98%, suitably 60–95%, preferably 75–90% and average pore size in the range 10–1000 µm, suitably 30–250 µm, preferably 50–150 µm. The lowermost zone, representing 0.05–1 mm in thickness, may be coated with a bioactive material such as hydroxyapatite to enhance integration with the underlying subchondral bone.

In the preferred embodiment for the replacement of the knee menisci, the overall dimensions of the first matrix component preferably correspond to the dimensions of the meniscal fragment to be replaced. The predominant orientation of the polymeric macrostructure of the first matrix component may be parallel to the surface of the construct in the outermost 100–300 µm of the construct corresponding to the superficial zone of the natural meniscus. The porosity within this region can be between 50–98%, suitably 60–95%, preferably 65–80% with pore size in the range 10–1000 µm, suitably 30–250 µm, preferably 50–100 µm. The central core of the polymeric macrostructure of the first matrix component may be predominantly radial in orientation with minor linking structures oriented at 90° to the predominant orientation. The porosity in this region may be between 50–98%, suitably 60–95%, preferably 75–90% with pore size in the range 10–500 µm, suitably 30–250 µm, preferably 50–150 µm.

The hydrated gel which forms the second matrix component may be a hydrated polymeric gel such as the hydrated gels of alginate, agarose, carrageenans, glycosaminoglycans, proteoglycans, polyethylene oxide or collagen. In many situations the hydrated gel may be alginate. Preferably, the hydrated gel is biodegradable or bioresorbable. Suitably, the second matrix component can withstand compressive loading.

Alginate is a polysaccharide, derived from brown seaweeds, composed of D-mannuronic and L-guluronic acid monosaccharide subunits. Whilst the sodium salt of alginate forms viscous solutions, alginate can form hydrated gels in the presence of divalent cations such as calcium due to cross linking through the negatively charged carboxyl groups residing on the L-guluronic acid residues. The viscosity of the uncrosslinked solutions and thereby the mechanical strength of crosslinked gels can be influenced by altering the average chain length of the alginate or by altering the proportion of D-mannuronic acid and L-guluronic acid residues within the polysaccharide. These factors may also influence the rate of resorption of the alginate.

The concentration of the hydrated gel forming the second matrix component may be heterogeneous within the macrostructure formed by the first matrix component of the implant. This can provide functionally graded mechanical properties throughout the depth of the implant.

The hydrated gel forming the second matrix component can be modified by the addition of factors, which are immobilized within the gels after cross-linking or which are contained within the hydrated fraction of the gel and are free to diffuse. These factors include collagen, hydroxyapatite, growth factors, cytokines, cell attachment factors, chemotactic factors, angiogenic factors and factors which may influence the attachment of the construct to the existing tissue such as hydroxyapatite, tissue transglutaminase and matrix degrading enzymes. The degree to which these factors are immobilised is dependent on the size and charge of the factor and the concentration and thereby pore size of the alginate gel. A particular example of this modification is the incorporation of collagen within the alginate gel in order to increase the overall collagen content of the composite device. This may be of particular importance in the preparation of devices for meniscal repair.

As discussed above, preferably both the first and second matrix components are resorbable and over a period of time can be resorbed and cleared in vivo by hydrolysis, enzymic degradation, depolymerisation and diffusion to be replaced by natural matrix components synthesised by the cells of the implant. In this manner, the original construct can be replaced by an entirely natural repair tissue with functional integrity which, due to the presence of cells and the appropriate mechanical and biochemical signals, can reach a stable equilibrium in terms of cell number, architecture and matrix turnover.

The animal cells in the implant can be autologous, allogeneic or xenogeneic with respect to the host, preferably the cells are autologous. Conveniently, the cells can be chondrocytes, fibrochondrocytes, fibroblasts, osteoblasts, or sub-populations thereof, which have a differentiated phenotype. Alternatively, precursors of the aforementioned cell types may be used which have the potential to differentiate into such cells.

The cells can be isolated from a tissue biopsy or from bone marrow, using methods common to those skilled in the art. If insufficient cell numbers are available at isolation the cells can be allowed to proliferate in tissue culture prior to seeding into the construct. During the proliferation phase the cells may be cultured as a monolayer on a tissue culture treated substrate and maintained in tissue culture medium such as Dulbeccos Modified Eagle's Medium supplemented with, for example, between 1 and 20% fetal calf serum or autologous human serum. Alternatively the cells may be cultured in serum free medium supplemented with mitogens on tissue culture plastic modified by the immobilisation of specific attachment factors. In another alternative approach, the differentiated cells may be seeded at a specified seeding density within alginate beads and cultured in tissue culture medium supplemented with serum or mitogenic growth factors. The cells may be isolated by dissolving the beads in a sodium citrate saline solution followed by collagenase digestion. These cells may be passaged subsequently by seeding and culture in alginate beads at the same seeding density as previously described. The cells may be cultured within a suitable rotating bioreactor.

The biomechanical implants of the present invention represent an improvement over the known devices of the prior art for at least the following reasons.

The interaction between the first and second matrix components can provide enhanced mechanical properties which are greater than the sum of the properties of the two components individually. In this manner, the implant mimics the physiochemical interaction within natural cartilaginous tissues.

The presence of immobilized cells within the second matrix component ensures a uniform cell density throughout the construct over an extended period of time. Cell density throughout the first matrix component can be varied by altering its porosity which permits heterogeneities in cell density to be achieved.

Contact inhibition of proliferation typically occurs for cells cultured as a monolayer and cells seeded onto a single factor scaffold such as that described in WO 90/12603 therefore reach a limiting cell number which does not fill the voids within the scaffold. Whereas the present invention allows for cells to be maintained in a 3-dimensional state which does not induce contact inhibition of proliferation to occur until the entire 3-dimensional volume is filled. In this way, a greater cell density is achieved or a lower initial seeding density may be used.

BRIEF DESCRIPTION OF THE FIGURES

Cell morphology is known to influence cell phenotype and the type, quantity and organisation of extracellular matrix produced by the cells. The present invention permits cells to be maintained in either a rounded or elongated morphology, thereby allowing control of cell phenotype to be achieved. The meniscus contains two sub-populations of cells, one which is elongated and fibroblastic in phenotype, the other rounded and chondrocytic in phenotype. The phenotypes are interchangeable by the use of appropriate cell culture conditions. The present invention permits the restoration of the two sub-populations by seeding cells onto the first matrix component and within the second matrix component.

The biomechanical implant of the present invention also permits the transfer of mechanical load applied to the construct to the cells seeded within it in a defined manner. The inherent mechanical integrity of the construct allows mechanical load to be applied either in vitro or in vivo. Different cellular strain regimes and mechanotransduction pathways can be induced by seeding the cells onto the first matrix component or within the second matrix component.

Furthermore, it is known that mechanical strain influences cell behaviour in many load-bearing connective tissue such as articular cartilage, meniscus, tendon, ligament, intervertebral disc, bone and skin. In many cases this phenomenon can be crucial to the maintenance of tissue structure and function. The exact mechanism by which cells sense and respond to strain, known as mechanotransduction, is unclear but is believed to include cell deformation, alterations in fluid pressure, streaming potentials, fluid flow, alterations in nutrient concentration and transport, alteration in pH and variations in the osmotic environment. The preferred embodiments of the present invention may induce alterations in cell behaviour in response to mechanical loading through many of the aforementioned mechanotransduction pathways. Mechanical loading may be applied to the cells within the construct prior to implantation using specially designed technologies or applied to the cells within the construct post implantation through defined exercise regimes or through externally applied regimes such as continuous passive motion regimes. Mechanical loading regimes, applied in a static or dynamic manner may take a variety of forms including, although by no means exclusively, uniaxial compression or tension or hydrostatic pressure. Static and dynamic peak strain amplitude may be in the range between 0.5–30%, suitably 1–25%, preferably 5–20% whilst dynamic frequencies should range from 0.001–10 Hz, suitably 0.01–5 Hz, preferably 0.1–3 Hz.

The are also several advantages in the application of mechanical strain which may be transferred to the cells within the construct prior to implantation.

Firstly, the use of optimal strain windows of biosynthetic response can quantitatively increase metabolic parameters known to influence the success of tissue engineered repair devices such as cell proliferation, proteoglycan synthesis and collagen synthesis.

Secondly, qualitative reorganisation and/or orientation of newly synthesised matrix components in response to strain may be induced which can provide anisotropy and, potentially, improved gross mechanical properties. Orientation of cells along strain fields may induce long-term production of oriented matrix. Oriented cell proliferation may also restore the cell architecture, such as columns which are a feature of articular cartilage and are important in the structural/functional relationship within the tissue. The cells in the implant may suitably possess a pre-implantation strain history and can therefore be adapted to respond to mechanical strain post-implantation.

According to a second aspect of the present invention there is provided a method of repairing damaged connective tissue, in which the method comprises the step of wholly or partially replacing the damaged tissue with a biomechanical implant as defined above.

This aspect of the present invention also contemplates the use of at least two matrix components the first matrix component having a porous macrostructure with the ability to withstand tensile or shear forces, the second matrix component being a hydrated gel which substantially fills the porous macrostructure of the first component and has the ability to withstand compressive loading, and a population of animal cells having a differentiated phenotype or having an undifferentiated phenotype with the potential to differentiate into such cells, in the preparation of a biomechanical implant for repair of damaged connective tissue.

The implant may be most applicable to tissues where there is a mechanical interaction in the loaded and unloaded state sufficient to set up an equilibrium between major matrix components, such as those with a mechanical function, where compression is the predominant type of loading. Suitable tissues for repair can include but are not limited to tissues such as cartilage, temperomandibular joint menisci, knee menisci and intervertebral discs.

According to a third aspect of the present invention, there is provided a biomechanical implant comprising at least two matrix components the first matrix component having a porous macrostructure with the ability to withstand tensile or shear forces, the second matrix component being a hydrated gel which substantially fills the porous macrostructure of the first component and has the ability to withstand compressive loading, the implant additionally comprising a population of animal cells having a differentiated phenotype or having an undifferentiated phenotype with the potential to differentiate into such cells, as a combined preparation for simultaneous, separate or sequential use in the preparation of a biomechanical implant for repair of damaged connective tissue.

According to a fourth aspect of the present invention, there is provided a method for the manufacture of a biomechanical implant as defined above, in which the method comprises the steps of:

(a) infiltrating a solution of the uncrosslinked precursor of the hydrated gel into the first matrix component, (b) crosslinking the gel in situ to form the second matrix component, (c) incorporating the cells into the matrix, and (d) applying mechanical loading.

Where the hydrated gel is alginate, a solution of sodium alginate at concentrations ranging from 0.5–10% (w/v), suitably, 1–8% (w/v), preferably 2–6% (w/v) may be prepared in water, salt solution or tissue culture medium. The solution can be infiltrated into the porosity of the first matrix component by diffusion, vacuum infiltration or centrifugation in a manner to ensure that all the pores are filled. Sodium alginate solutions swell, markedly, when separated from an isotonic saline solution by a permeable barrier. Typically, a 50% increase in weight occurs during the first 4 hours of water uptake. In this manner sodium alginate entrapped within the first matrix component can be immersed in saline and will exert a physicochemical swelling pressure which is resisted by the first matrix component thereby setting up tensile forces within the first matrix component in the unloaded state. This relies upon the ability of the first matrix component to resist swelling and not exhibit marked swelling in its own right. This ability is determined by the structural composition of the first matrix component.

The composite construct can then be immersed in a solution containing a salt of a divalent cation to induce crosslinkage of the alginate in situ to form a hydrated gel. The most preferred crosslinking solution contains calcium chloride at concentrations ranging from 10–500 mM, suitably 25–250 mM, preferably 50–150 mM. In this manner the alginate gel can be immobilized within the porosity of the first matrix component.

The cells can be incorporated into the construct in a number of ways, which include direct attachment to the first matrix component, addition of the cells to the solution of the second matrix component prior to infiltration into the first matrix component or attachment of the cells to the first matrix component and immobilisation of cells within the second matrix component to produce two sub-populations of cells within the construct with different morphologies.

Direct attachment of the cells to the first matrix component can be achieved by the addition of a suspension of cells in medium to a suitably prepared piece of the first matrix component. Infiltration of the cell suspension into the porosity of the first matrix component can draw cells into it which subsequently attach and spread on the polymeric surface of the first matrix component. The cells may assume a flattened or elongated morphology. Subsequent culture in suitable tissue culture medium may cause proliferation and migration of the cells which can lead to the formation of a uniform covering of cells over the entire surface of the first matrix component. At any stage after the cells have attached to the first matrix component, infiltration and crosslinking of the second matrix component can be performed.

Addition of the cells to the solution of the second matrix component prior to infiltration into the first matrix component achieves incorporation of the cells into the matrix as the infiltration draws the cells into the porous structure of the first matrix component in association with the second matrix component. The cells can become immobilised within the hydrated gel after crosslinking of the second matrix component. Thereby the cells may retain a rounded morphology and remain unattached directly to the first matrix component.

Attachment of a proportion of cells to the first matrix component and immobilisation of cells within the second matrix component can produce two sub-populations of cells within the construct with different morphologies. Alternatively, expanded sub-populations of cells, such as cells isolated from the superficial and deep zones of articular cartilage, may be seeded in either or both matrix components within the distinct zones of the implant. The construct can be implanted directly after cell seeding or the construct containing cells can be maintained in tissue culture to allow the synthesis of extracellular matrix components by the cells and proliferation of the cells prior to implantation. Defined loading regimes can be applied to the cells within the construct during the culture phase using specially designed technologies as described in the examples.

Preferred features and characteristics of the second and subsequent aspects are as for the first aspect mutatis mutandis.

The invention will now be described by way of example with reference to the accompanying Examples and drawings which are provided for the purposes of illustration and neither of which are to be construed as being limiting on the present invention. In the following description, reference is made to a number of drawings, in which.

EXAMPLES

Example (1) Cell Isolation and expansion in culture

Chondrocytes were isolated from either bovine cartilage or human cartilage obtained after amputation due to osteosarcoma. Meniscal cells were isolated from human knee menisci obtained after amputation due to osteosarcoma. The cartilage or meniscal tissue was cut into cubes of no more than 2 mm$^3$ and sequentially digested with 1% (w/v) pronase (BDH Ltd. Poole, England) in Dulbecco's Modified Eagles Medium, 2% HEPES buffer, 1% Glutamine and 1% penicillin/streptomycin (referred hereafter as DMEM) containing 20% FCS for 1 h at 37° C. followed by collagenase Type 1A (Sigma) in DMEM +20% FCS for 2h at 37° C. The enzyme concentration (i.u./ml) is optimised for each new batch of collagenase. Debris was removed from the cell containing medium by filtration through a nylon sieve (Falcon 70 µm pore size) and the cells separated by centrifugation at 1000 g for 5 minutes. The cell pellet was washed x2 with DMEM+20% FCS and resuspended in an appropriate volume of medium. Cell density and viability was determined by the Trypan Blue exclusion test.

Where necessary, the cell population will be expanded to the desired number by repeat passage. Cells will be cultured as a monolayer in tissue culture flasks in DMEM+10% FCS at 37° C./5%CO$_2$ with medium changes every two days. At confluence the cells will be lifted with 0.2% trypsin/EDTA and divided into three flasks for further culture.

Example (2) Seeding of fibrochondrocytes into collagen gels

Figure 1:
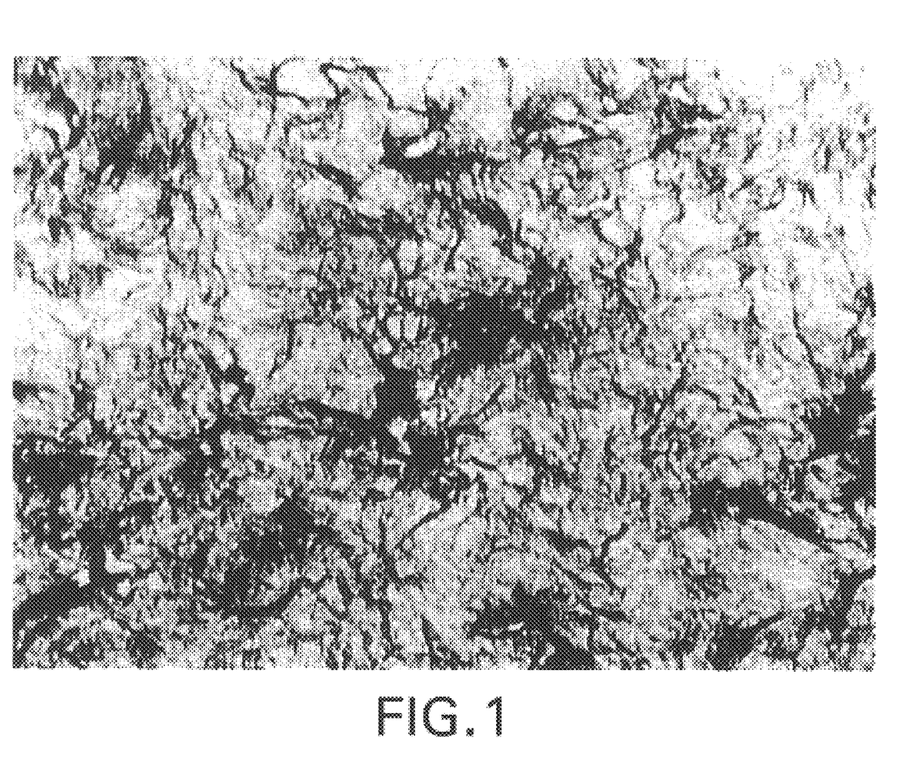
FIG. 1 shows a photomicrograph of a haematoxylin and eosin stained section prepared from a meniscal fibrochondrocyte seeded collagen gel fixed immediately after casting. Magnification X250.

Human fibrochondrocyte seeded collagen gels were prepared by mixing 12 ml of double strength Dulbeccos Modified Eagle Medium (DMEM, Gibco, Paisley, UK), 3 ml of a cell suspension (1×10$^6$ cell/ml in DMEM), 3 ml foetal calf serum (FCS, Gibco, Paisley, UK), 3 ml 0.1 M NaOH and 9 ml collagen solution (3 mg/ml collagen type I in 0.5M acetic acid, ICN, Paisley, UK). All components were maintained at 4° C. during mixing. Aliquots (1.5 ml) of the solution were added to wells and gelled at 37° C./5%CO$_2$ for 30 minutes. The gels were maintained at 37° C./5%CO$_2$ in DMEM+10% FCS+150 µg/ml ascorbate with medium changes every 2 days. Cell-induced contraction of the gel occurred during the first 3 days. Histology revealed the presence of cells with typical fibroblastic morphology evenly distributed within a disorganised fibrous collagen matrix, as shown in FIG. 1.

Example (3) Seeding of chondrocytes onto collagen sponges

Figure 2:
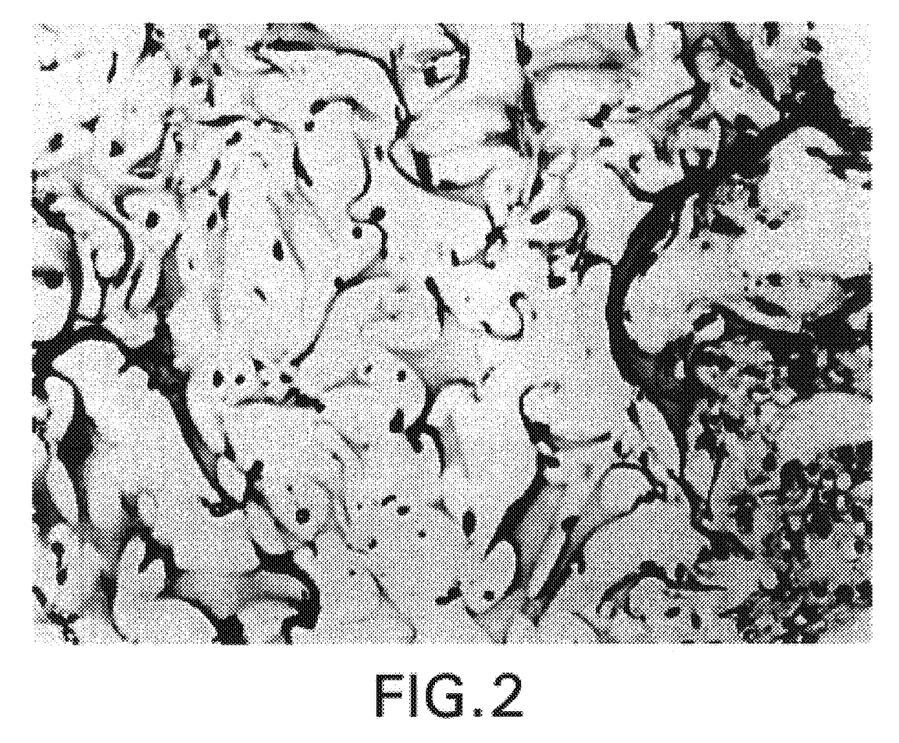
FIG. 2 shows a photomicrograph of a haematoxylin and eosin stained section prepared from a collagen sponge construct seeded with bovine chondrocytes and cultured for 14 days. Magnification X250.

Bovine chondrocytes were seeded onto collagen sponges by absorption. Cylinders of absorbable sponge 3 mm thick and 6 mm in diameter (Helistat® Colla-Tec, Inc. U.S.A.) were cut. Medium (100 µl) containing 1.5×10$^7$ cells/ml was either added dropwise to the surface of the dry matrix or the sponge was immersed in cell containing medium. The sponges containing cells were cultured in DMEM+20%FCS for up to 24 days with medium changes every two days. Histology using haematoxylin and eosin staining revealed the presence of clusters of chondrocytes within the sponge matrix. The majority of cells exhibited rounded morphology although a proportion were flattened or fibroblastic in appearance as shown in FIG. 2. The density was not homogeneous with the greatest proportion of cells at the periphery of the sponge. Evidence of synthesis of proteoglycan rich matrix around the cells was noted.

Example (4) Seeding of chondrocytes in alginate

Figure 3:
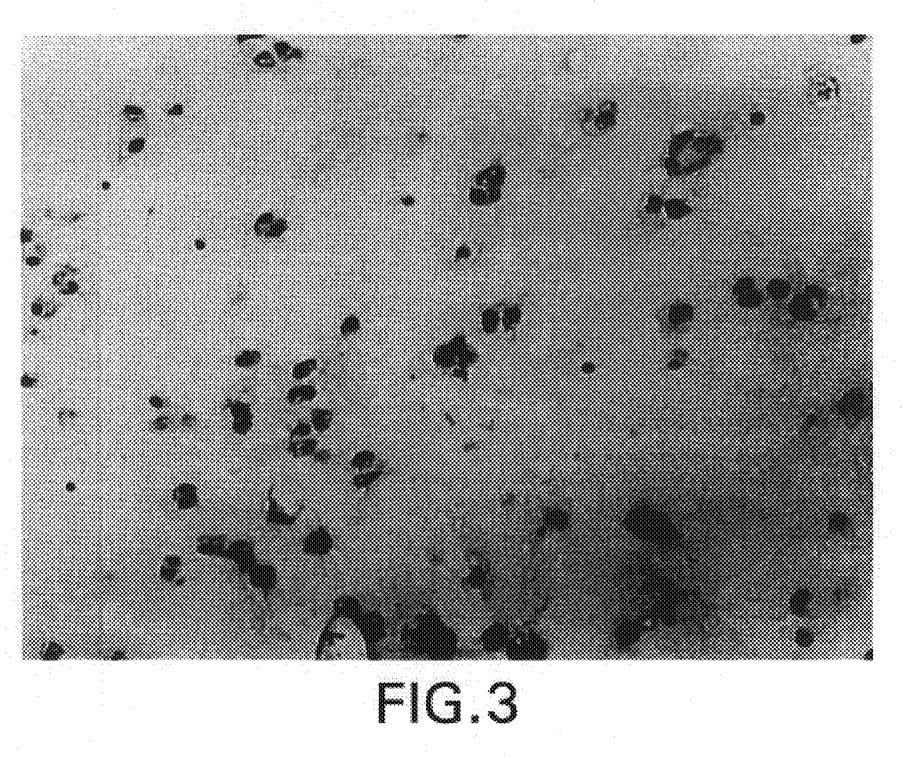
FIG. 3 shows a photomicrograph of a haematoxylin and eosin stained section prepared from a bovine chondrocyte seeded alginate construct which had been cultured for 7 days. Magnification X250.

An equal volume of 4% (w/v) alginate (Kelco International Ltd. Waterfield, Tadworth, Surrey, UK) in Earle's buffered salt solution (EBSS) was mixed with 1.6×10$^7$ cells/ml in DMEM containing 20% FCS by gentle agitation. Cross-linking of the alginate suspension was effected by dialysis against a solution of 100 mM CaCl$_2$ in DMEM/10% FCS. The crosslinked gel constructs were cultured in DMEM+20% FCS+150 µg/ml ascorbate for up to 24 days with medium changes every 2 days. After 6 days in culture a proportion of the chondrocytes within the alginate gel had undergone proliferation to form small clusters as shown in FIG. 3. The cells retained their original rounded morphology and synthesised a 'halo' of cartilaginous matrix.

Example (5) Seeding of chondrocytes into agarose

Figure 4:
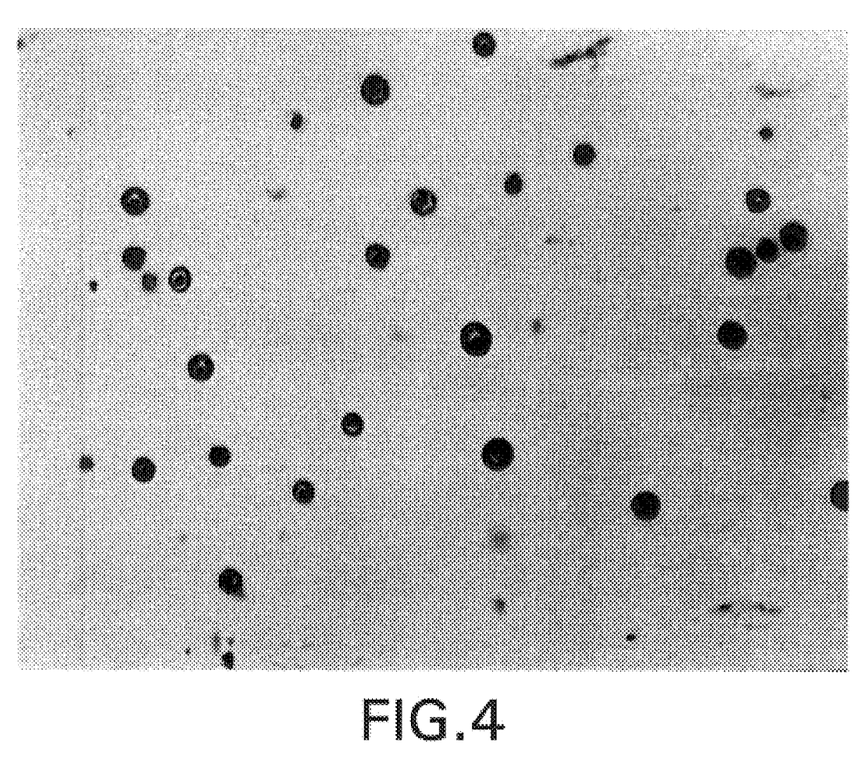
FIG. 4 shows a photomicrograph of a haematoxylin and eosin stained section prepared from a bovine chondrocyte seeded agarose construct which had been cultured for 3 days. Magnification X250.

During preparation of a cell suspension containing 2×10$^7$ cells/ml, a 6% suspension of agarose (type VII, Sigma, Poole, England) in distilled water was melted by autoclaving and subsequently cooled to 37° C. The chondrocyte suspension was added to an equal volume of agarose to give a final concentration of 1×10$^7$ cells/ml in 3% agarose. The agarose suspension was plated in a tissue culture dish and gelled at 4° C. for 20 minutes. Cylindrical constructs, 5 mm diameter×5 mm height were formed and cultured in DMEM+20% FCS+150 µg/ml ascorbate for up to 24 days. Histology using haematoxylin and Safranin-O staining revealed the presence of an even distribution of cells with a rounded morphology as shown in FIG. 4. After 3 days a significant 'halo' of cartilaginous matrix was present around the cells and cell clusters formed by proliferation were noted after 6 days.

Example (6) Preparation of two component constructs by diffusion techniques

Figure 5:
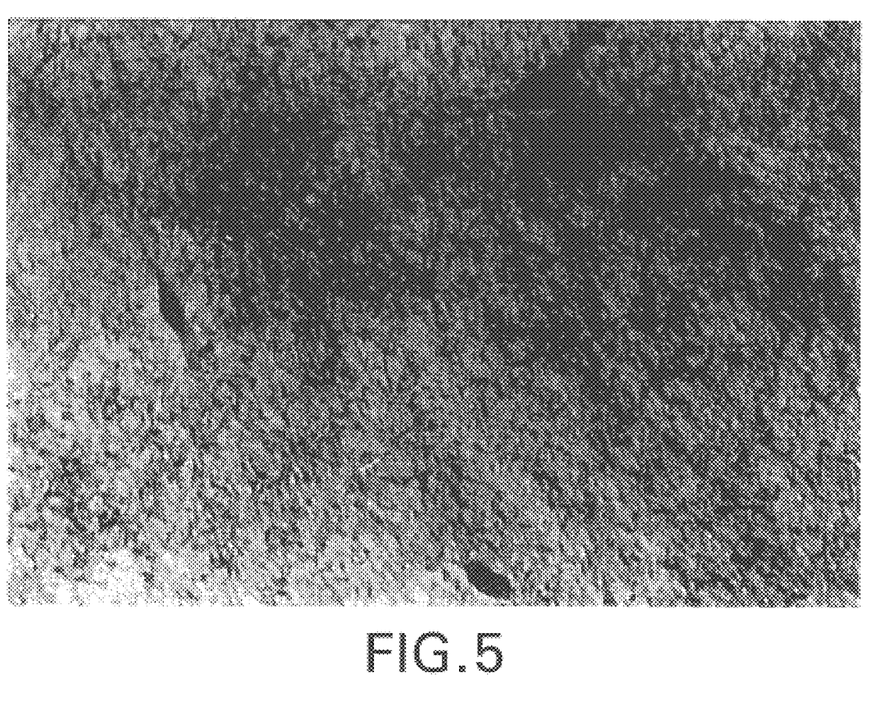
FIG. 5 shows a photomicrograph of a haematoxylin and eosin stained section prepared from a collagen gel/alginate composite construct seeded with meniscal fibrochondrocytes which had been cultured for 3 days. Magnification X500.

Fibrochondrocyte seeded collagen gels were cast as described in example 2 and cultured for 24 hr. The gels were placed in a suspension of 2% (w/v) alginate in DMEM+10% FCS:EBSS (1:1). The alginate was crosslinked by dialysis against a solution of 100 mM CaCl$_2$ in DMEM/10% FCS. The constructs were cultured in DMEM+10% FCS+150 μg/ml ascorbate for up to 24 days with medium changes every 2 days. Histology revealed the presence of evenly distributed cells with a fibroblastic morphology throughout the composite as shown in FIG. 5. Alginate content was inhomogeneous with greater concentration at the periphery of the construct.

Figure 6:
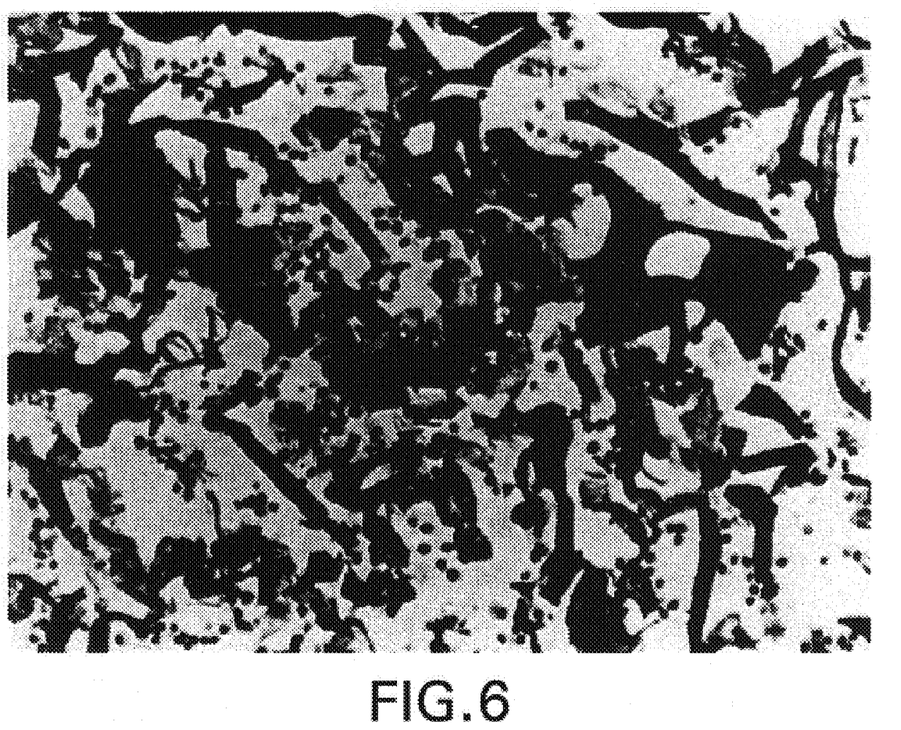
FIG. 6 shows a photomicrograph of a haematoxylin and eosin stained section prepared from a collagen sponge/alginate composite construct seeded with chondrocytes which had been cultured for 1 day. Magnification X250.

Collagen sponges with or without prior culture were infiltrated with 2.0% (w/v) alginate containing 1.5×10$^7$ chondrocytes/ml in DMEM+20% FCS:EBSS (1:1) or 2% (w/v) agarose type VII containing 4×10$^6$ cells/ml in DMEM+20% FCS:EBSS (1:1) by dropwise addition to the surface of the sponge. The alginate was crosslinked by bathing the construct in a solution of 100 mM CaCl$_2$ in DMEM/10% FCS. Agarose containing constructs were gelled by incubation at 4° C. for 30 minutes. The constructs were cultured in DMEM+20% FCS+150μg/ml ascorbate for up to 24 days with medium changes every 2 days. Cells, associated with the agarose were found evenly distributed within the porous microstructure of the collagen sponge and exhibited rounded morphology as shown in FIG. 6. There was evidence of cartilaginous matrix production around the cells.

Example (7) Preparation of two component constructs by Vacuum Infiltration

Figure 7:
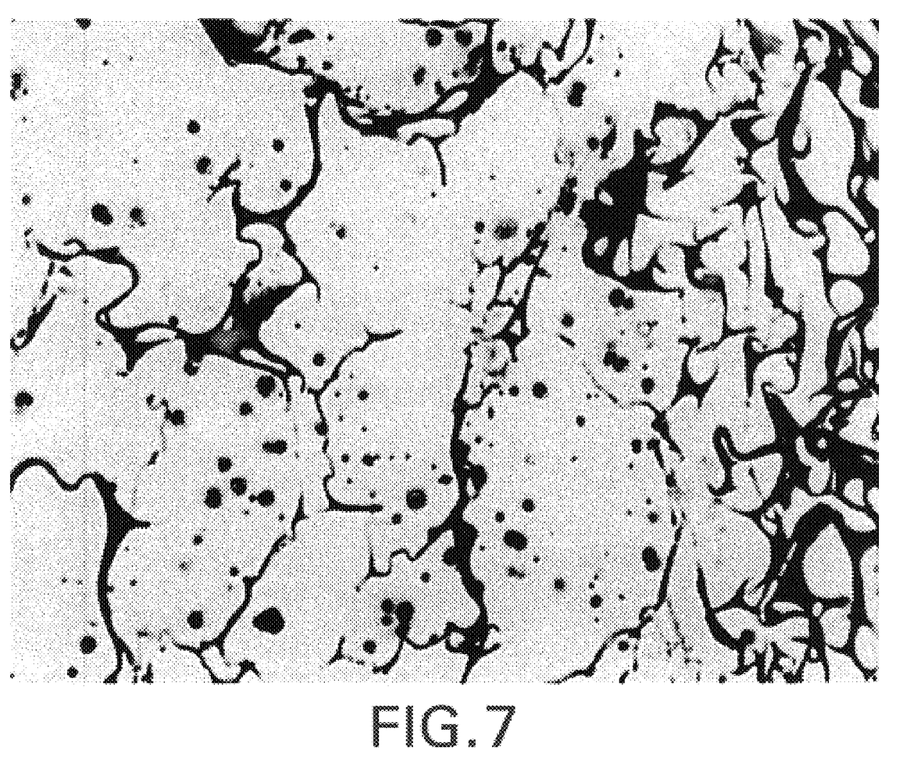
FIG. 7 shows a photomicrograph of a haematoxylin and eosin stained section prepared from a collagen sponge/agarose composite construct seeded with chondrocytes which had been cultured for 7 days. Magnification X250.

Collagen gels or sponges 6 mm diameter with or without prior culture of cells were placed in a 96 well sterile vacuum manifold plate (Multiscreen® Millipore UK), 100 μl of 2% (w/v) alginate in DMEM+10% FCS:EBSS (1:1) containing 1.5×10$^7$ cells/ml was layered on top of the collagen gel or sponge. A gentle vacuum was applied to incorporate the alginate and cells into the collagen gel or sponge. Crosslinking of the alginate was effected by bathing the construct in a solution of 100 mM CaCl$_2$ in DMEM/10% FCS. An even distribution of cells was seen throughout the porous microstructure of the collagen sponge. The cells were associated with the alginate which was also evenly distributed and the cells possessed a rounded morphology as shown in FIG. 7.

Example (8) Preparation of two component constructs by Low Speed Centrifugation

Collagen gels or sponges with or without prior culture of cells were placed in wells of a tissue culture plate. 2% alginate in Earle's buffered salt solution (EBSS) containing 4×10$^6$ cells/ml in DMEM and 10% FCS was gently layered on top of the collagen gel or sponge. The tissue culture plate was centrifuged at 100 g for 5 minutes to incorporate the alginate and cell suspension within the collagen gel or sponge. Crosslinking of the alginate was effected by bathing the construct in a solution of 100 nM CaCl$_2$ in DMEM/10% FCS.

Example (9) Mechanical testing of two component constructs and their components

The mechanical characteristics of the collagen gels and composites were evaluated. Uniformly sized cores of each material to be tested were mounted between two large plattens and tested to failure in compression at a crosshead speed of 1 mm/min using a universal testing machine (Instron Model 1122). The tangent modulus, an estimate of the material stiffness, was calculated from the linear region using the following equation:

$$modulus(MPa) = \frac{Ft}{dtA}$$

Where F=compressive force; t=Original thickness of material; dt=change in thickness; A=sample cross-sectional area. Another parameter, the equilibrium modulus, is calculated from a load relaxation experiment conducted at a prescribed strain of 20%.

Composite constructs consisting of 2% Keltone HV alginate infiltrated by vacuum into collagen sponges had a significantly greater tangent modulus than either collagen or alginate alone, indicating physicochemical interaction between the components as shown in Table 1.

TABLE 1

Mechanical evaluation of single and two component collagen and alginate constructs.

| Construct | Tangent Modulus | Equilibrium Modulus |
| --- | --- | --- |
| Collagen sponge/alginate construct | 85 kPa | 32 kPa |
| Collagen sponge construct | <1 kPa | <1 kPa |
| Alginate construct. | 25 kPa | 9 kPa |

Example (10) Mechanical Stimulation of cells in Hydrated Gels

Figure 8A:
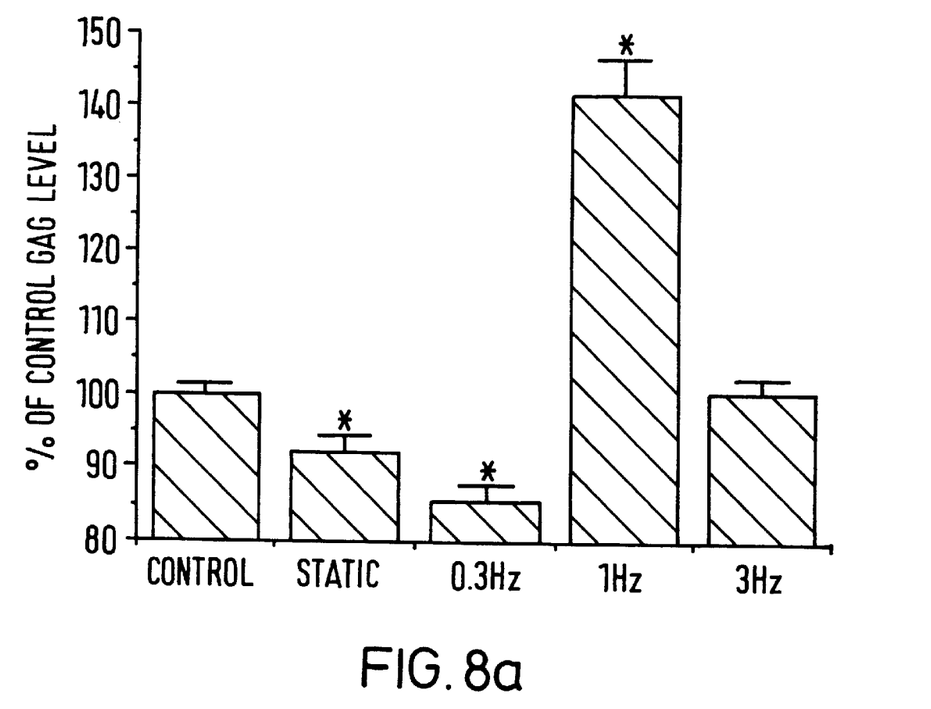
FIG. 8a shows a graph representing glycosaminoglycan synthesis by chondrocytes seeded in agarose constructs and subjected to 15% gross compressive strain at various frequencies for 48 hr. The values have been normalised to unstrained control levels (100%).
Figure 8B:
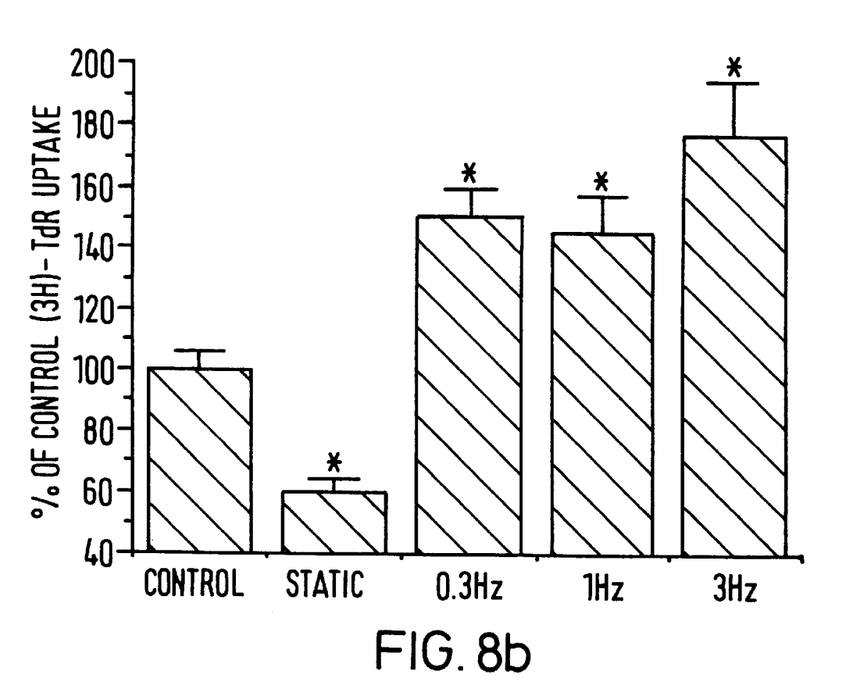
FIG. 8b shows a graph representing [$^3$H]-thymidine incorporation by chondrocytes seeded in agarose constructs and subjected to 15% gross compressive strain at various frequencies for 48 hr. The values have been normalised to unstrained control levels (100%).

A specially designed cell straining apparatus (Dartec Ltd, Stourbridge, UK) described in the literature was used to apply compressive strain to chondrocytes seeded in agarose as described in example 6 (Lee, D. A., and Bader, D. L., Journal of Orthopaedic Research 15 (2) 181–188 (1997). The constructs were subjected to a compressive strain amplitude of 15% at three dynamic frequencies (0.3 Hz, 1 Hz, 3 Hz). In addition static compressive strain was applied. Controls were unstrained. The compressive strain was applied for 48 hr and GAG synthesis, cell proliferation and total protein synthesis in response to strain were assessed. GAG synthesis was stimulated at 1 Hz as shown in FIG. 8a, whilst cell proliferation was stimulated by all of the dynamic strain regimes as shown in FIG. 8b.

Figure 9:
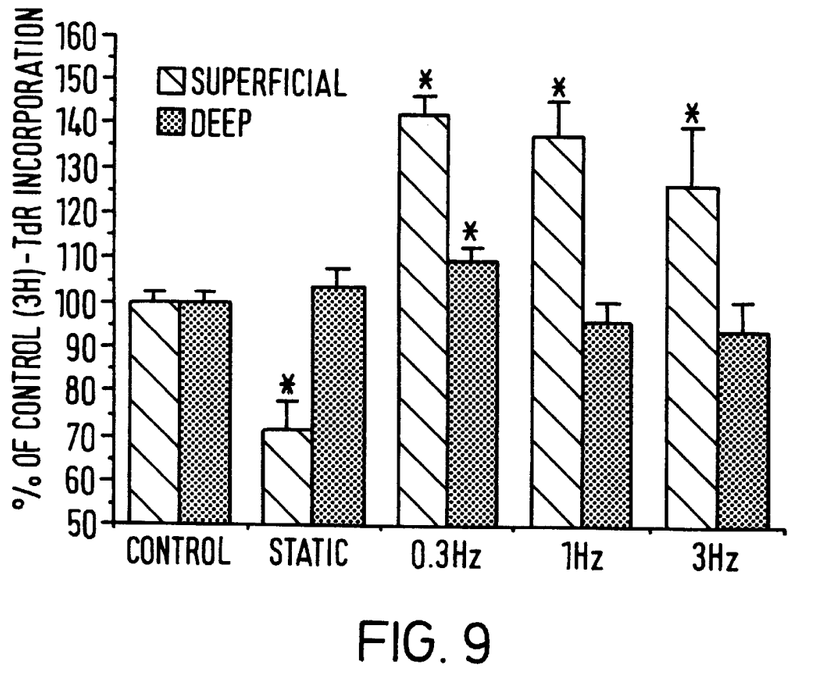
FIG. 9 shows a graph representing [$^3$H]-thymidine incorporation by chondrocytes isolated from the superficial and deep zones of cartilage and seeded in agarose constructs and subjected to 15% gross compressive strain at various frequencies for 48 hours. The values have been normalised to unstrained control levels (100%).

Example (11) Mechanical stimulation of chondrocyte subpopulations in hydrated gels Chondrocytes were isolated, separately, from the superficial and deep zones of bovine cartilage and seeded within 3% agarose constructs. The constructs were subjected to a compressive strain amplitude of 15% at three dynamic frequencies (0.3Hz, 1 Hz, 3 Hz). In addition, static compressive strain was applied. Controls were unstrained. The compressive strain was applied for 48 hours and cell proliferation in response to strain was assessed. Cell proliferation was stimulated in superficial zone cells by all of the dynamic strain regimes as shown in FIG. 9. By contrast, deep zone cells were unaffected by both static and dynamic strain regimes as shown in FIG. 9.

What is claimed is:

1. A method for the manufacture of a biochemical implant comprising at least two matrix components, the first matrix component having a porous macrostructure with the ability to withstand tensile or shear forces, the second matrix component being hydrated gel which substantially fills the porous macrostructure of the first component and exerts a swelling pressure, the implant additionally comprising a population of animal cells having a differentiated biomechanical phenotype or having an undifferentiated phenotype with the potential to differentiate into such cells, in which the method comprises:

(a) infiltrating a solution of the uncrosslinked precursors of the hydrated gel into the first matrix component;

(b) crosslinking the gel in situ to form the second matrix component;

(c) incorporating the cells into the matrix defined by the first and second matrix components; and (d) applying a mechanical loading.

2. A method as claimed in claim 1, in which the uncrosslinked precursors of the hydrated gel are infiltrated into the first matrix component by diffusion, vacuum infiltration or centrifugation.

3. A method as claimed in claim 1, in which the cells are incorporated into the matrix (i) by direct attachment to the first matrix component, (ii) by addition of the cells to the solution of the second matrix component prior to infiltration into the first matrix component, or (iii) by attachment of the cells to the first matrix component and immobilization of cells within the second matrix component.

4. A method as claimed in claim 1, in which the implant is a fill or partial replacement for a tissue where there is a mechanical interaction in both the loaded and unloaded states sufficient to set up an equilibrium between major matrix components.

5. A method as claimed in claim 4, in which the tissue comprises cartilage, temperomandibular joint meniscus, knee meniscus or an intervertebral disc.

6. A method as claimed in claim 1, in which the first matrix component is composed of a biodegradable or bioresorbable polymer.

7. A method as claimed in claim 6, in which the biodegradable or bioresorbable polymer comprises collagen, gelatin, poly-L-lactic acid, poly-glycolic acid, polycaprolactone, polyhydroxybutarate, polyanhydrides or a copolymer thereof.

8. A method as claimed in claim 7, in which the biodegradable or bioresorbable polymer is modified by crosslinking agents.

9. A method as claimed in claim 6, in which the first matrix component further comprises a coating of hydroxyapatite, fibronectin, collagen, vitronectin, hyaluronan, proteoglycans, glycosaminoglycans or RGD (Arg-Gly-Asp).

10. A method as claimed in claim 9, in which the coating is restricted to specified portions of the implant.

11. A method as claimed in claim 6, in which the first matrix component has a groove or microporosities in the range of 0.1–50 $\mu$m.

12. A method as claimed in claim 6, in which the polymeric components forming the first matrix component have an average pore size ranging from 10–1000 $\mu$m.

13. A method as claimed in claim 1, which is in the form of woven or non-woven fibres, sponges, foams or a series of plates or sheets joined by interconnecting strands, fibres or adjoining plates.

14. A method as claimed in claim 1, in which the hydrated gel which forms the second matrix component is hydrated polymeric gel.

15. A method as claimed in claim 14, in which the hydrated polymeric gel is biodegradable or bioresorbable.

16. A method as claimed in the claim 14, in which the hydrated polymeric gel comprises alginate, agarose, carrageenans, glycosaminoglycans, proteoglycans, polyethylene oxide or collagen monomers.

17. A method as claimed in claim 14, in which the hydrated gel is heterogenous in nature.

18. A method as claimed in claim 14, in which the hydrated gel is cross-linked.

19. A method as claimed in claim 14, in which the hydrated gel further comprises collagen, hydroxyapatite, growth factors, cytokines, cell attachment factors, chemotactic factors, angiogenic factors or enzymes.

20. A method as claimed in claim 1, in which the animal cells in the implant are autologous, allogenic or xenogenic with respect to the host.

21. A method as claimed in claim 20, in which the cells comprise chondrocytes, fibrochondrocytes, fibroblasts or osteoblasts, or sub-populations thereof or precursors thereof.

22. A method as claimed in claim 20, in which the cells are derived from a tissue biopsy.

* * * * *